United States Patent
Donahue et al.

(10) Patent No.: US 6,586,208 B2
(45) Date of Patent: Jul. 1, 2003

(54) USE OF SUPPRESSOR TRNA'S TO REGULATE CYTOTOXICITY DURING THE PRODUCTION OF RECOMBINANT GENE PRODUCTS

(75) Inventors: Brian A. Donahue, Los Altos, CA (US); Stephen F. Hardy, San Francisco, CA (US); Richard O. Snyder, Gainesville, FL (US)

(73) Assignee: Cell Genesys, Inc., South San Francisco, CA (US)

( * ) Notice: Subject to any disclaimer, the term of this patent is extended or adjusted under 35 U.S.C. 154(b) by 0 days.

(21) Appl. No.: 09/784,130

(22) Filed: Feb. 16, 2001

(65) Prior Publication Data

US 2002/0076808 A1 Jun. 20, 2002

Related U.S. Application Data

(63) Continuation of application No. PCT/US99/16726, filed on Aug. 20, 1999.
(60) Provisional application No. 60/097,328, filed on Aug. 20, 1998.

(51) Int. Cl.[7] ............................. C12N 7/01; C12N 5/10; C12N 15/86; C12N 15/861; C12P 21/00
(52) U.S. Cl. ................... 435/69.1; 435/235.1; 435/325; 435/320.1
(58) Field of Search ............................... 435/69.1, 325, 435/235.1, 320.1, 975; 536/24.1

(56) References Cited

U.S. PATENT DOCUMENTS 4,687,737 A * 8/1987 Sharp et al. ............... 435/69.1
5,679,566 A * 10/1997 He et al. .................... 435/325
6,309,830 B1 * 10/2001 Panchal et al. ................ 435/6

FOREIGN PATENT DOCUMENTS

| EP | 0823480 | 2/1998 |
|---|---|---|
| WO | 9201070 | 1/1992 |

OTHER PUBLICATIONS

Wang et al. Cancer Gene Ther. (2, 4, 322) 1995.*
Human gene therapy (United States) Dec. 1995, 6 (12) p1575–86.*
Virology, vol. 184, pp. 310–318, (1991). Smuda et al. "Adeno–Associated Viruses Having Nonsense Mutations in the Capsid Genes: Growth in Mammalian Cells Containing an Inducible Amber Suppressor."
Virology, vol. 171, pp. 239–247, (1989). Chejanovsky et al. "Replication of a Human Parvovirus Nonsense Mutant in Mammalian Cells Containing an Inducible Amber Suppressor."
J. Virology, vol. 70, No. 1, pp. 559–565, (1996). Yeh et al. "Efficient Dual Transcomplementation of Adenovirus E1 and E4 Regions from a 293–Derived Cell Line Expressing a Minimal E4 Functional Unit."
J. Virology, vol. 70, No. 9, pp. 6497–6501 (1996). Brough et al. "A Gene Transfer Vector–Cell Line System for Complete Functional Complementation of Adenovirus Early Regions E1 and E4."

* cited by examiner

Primary Examiner—Mary E. Mosher
(74) Attorney, Agent, or Firm—Linda R. Judge, Esq.; Steven B. Kelber; Piper Rudnick LLP

(57) ABSTRACT

Suppressor tRNA's are used to regulate expression of transgenes that are toxic, or the expression thereof requires a factor that is toxic, to the host cell.

25 Claims, 16 Drawing Sheets

```
        HindIII
           |   AflII
               |
aagcttctttaagGTAGTCGTGGCCGAGTGGTTAAGGCGATGGACTCTAAATCCATTGGGGTCTCCCCGCGCAGGTTCGAA
ttcgaagaattcCATCAGCACCGGCTCACCAATTCCGCTACCTGAGATTTAGGTAACCCCAGAGGGGCGCGTCCAAGCTT
           1                              2                                    3
                BamHI
                  |
TCCTGCCGACTACGCCAtggttttttgctccggatcc
AGGACGGCTGATGCGGTaccaaaaacgaggcctagg
                                   4
```

FIG. 3C

```
                              Fnu4HI
             SpeI             BspWI
      Sau3AI                  McrI
      MboI                    GdiII
      DpnII                   EagI
      DpnI                    EaeI
      AlwI                    NotI
      NlaIV                   Fnu4HI        PvuII
      BstYI            RmaI   HaeIII        AluI
      BamHI            XbaI   BsiEI         NspBII
      AlwI      RmaI          BsrBI         MspAII
       ||        ||      ||   | ||||         ||
     gggggatccactagttctagagcggccgccacAGCTGA    118
     cccccctaggtgatcaagatctcgccggcggtgTCGACT
       ||        ||      ||   | ||||    *    ||
       84        91     100                  112
       84              96    103              112
       84              97     104              113
       84                    102              112
       85                    102
       85                    103
       85                    103
       85                    103
       85                    103
                  90          105
                              105
```

USE OF SUPPRESSOR TRNA'S TO REGULATE CYTOTOXICITY DURING THE PRODUCTION OF RECOMBINANT GENE PRODUCTS

The instant application is a continuation of PCT Ser. No. US99/16726 filed Aug. 20, 1999, which claims benefit to U.S. Ser. No. 60/097,328 filed Aug. 20, 1998.

BACKGROUND OF THE INVENTION

The production of desirable genetically engineered products can be less than efficient because the gene product itself or accessory molecules required for the proper production of the genetically engineered product of interest can be toxic to the host cell. For example, the rep proteins of adeno-associated virus (AAV), which are necessary for the integration and replication of the AAV genome in the host cell, often are toxic to the host cell and to, for example, the helper adenovirus.

Other examples of gene products which are used commonly in the art of genetic engineering and which are toxic to host cells are the E4 ORF6 protein of adenovirus, the VSV-G gene product of vesicular stomatitis virus and the HIV tat gene product.

SUMMARY OF THE INVENTION

The first object of the instant invention is to provide a method for expressing a recombinant gene product in a host cell under conditions that minimize exposure of the host cell to any foreign elements or products thereof, whether endogenous or not, that may be toxic to that host cell. The method relies on the use of a termination codon introduced into the coding sequence of a gene encoding a toxic protein and a sufficient amount of complementing suppressor tRNA's to overcome the presence of the termination codon engineered into the coding sequence of the gene encoding the toxic gene product, as well as releasing factors, termination factors and so on that normally interact with termination codons, to regulate expression of the toxic gene product. The toxic protein may be the product of interest or may be a protein required for efficient expression of the desired gene product of interest. The genes coding for the molecules that are toxic to the host cell are configured to contain one or more termination codons. Multiple toxic proteins can be manipulated in that fashion in a single cell. Also, multiple toxic proteins may be regulated by a single species of suppressor tRNA by introducing a termination codon at the same amino acid residue in the plural toxic proteins. Sufficient amounts of the suppressor tRNA's are made available in the host cell, for example, by transfecting the host cell with adenoviral vectors carrying the tRNA coding sequence.

Yet another object of the instant invention is to provide a method for minimizing the exposure of a host cell to the toxic adeno-associated virus (AAV) rep and cap proteins by introducing termination codons into the coding sequence of, for example, a rep gene, and using sufficient amounts of complementing suppressor tRNA's to overcome the presence of the termination mutation and endogenous termination factors, to therefore regulate the expression of that rep gene carrying the termination codon. The suppressor tRNA's can be targeted to one, two, three or four of the rep proteins. Moreover, the suppressor tRNA's can be directed to any amino acid codon. A suitable target is serine that appears in all four rep proteins. In that way, only a single species of suppressor tRNA would be required to regulate the expression of the four rep proteins.

Yet another object of the instant invention is to provide specific nucleic acid constructs, cells, vectors and the like for regulating the expression of toxic gene products in a host cell, such as the rep protein in the production of recombinant AAV.

Those and other objects have been achieved by the development of materials and methods for regulating the expression of toxic gene products that limit the establishment and productivity of a host cell in the production of recombinant gene products. For example, termination codons can be engineered into the coding sequence of a gene that encodes a toxic gene product. Then a suppressor tRNA which recognizes the termination codon and carries an aminoacyl group and thus incorporates an amino acid into the growing polypeptide instead of resulting in termination of translation is used. The suppressor tRNA complements the termination mutant and enables translation to occur when expression of the foreign gene product is desired. A suitable target is the rep protein of AAV that is toxic to the host cell. Yet another suitable target is the cap protein of AAV.

The instant method can be applied to regulate a number of genes which encode products which are toxic to host cells and which are commonplace in the art of recombinant nucleic acid technology.

BRIEF DESCRIPTION OF THE DRAWINGS

FIGS. 3A–3D construction of a plasmid encoding an amber suppressor tRNA gene FIG. 3A The amber suppressor tRNA gene was derived from a human serine tRNA gene (shown in capital letters) in which the serine anticodon was replaced with the amber anticodon (underlined). Linker regions (shown in lower case) were situated on either side of the tRNA gene. The 5' linker consists of the HindIII and AflII recognition sequences and the 3' linker consists of a 10 base spacer followed by the BamHI recognition sequence. The 116 bp DNA fragment (SEQ ID NO:8) was generated by forming a scaffold with four oligonucleotide primers (shown in bold) followed by PCR amplification. FIG. 3B The 116 bp tRNA fragment was digested with BamHI and then ligated to the 3332 bp EcoRV-BamHI fragment of pAdlox 12 to form plasmid pAdlox 12 sup tRNA. FIGS. 3C and 3D depict pAdlox 12, which is pAdlox (Hardy et al., 1997) with the expression cassette removed and replaced with a polylinker. Specifically, the sequence between PvuII and ClaI was removed from pAdlox and replaced by the polylinker sequence depicted in FIGS. 3C and 3D (SEQ ID NO:9).

DETAILED DESCRIPTION OF THE INVENTION

Figure 1:
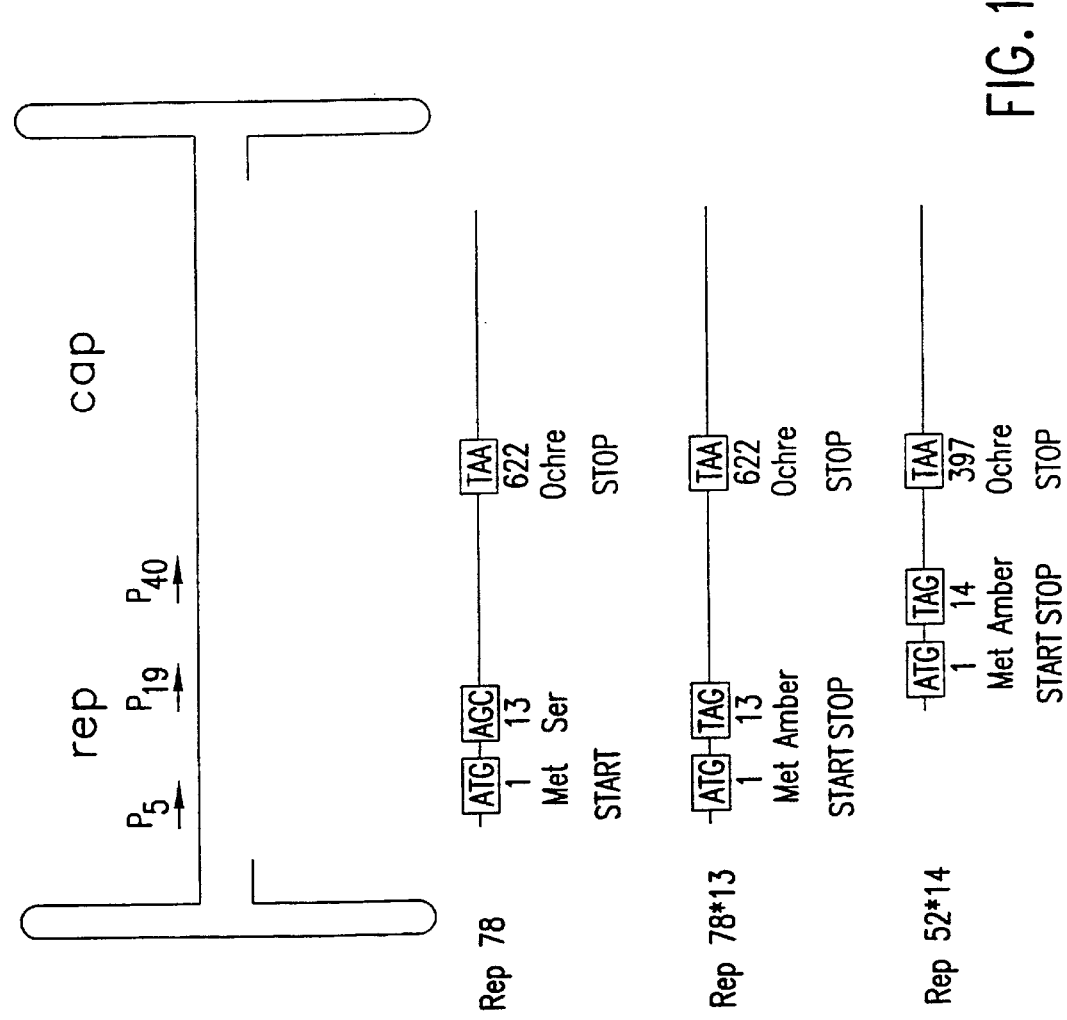
FIG. 1 Scheme for inactivating the toxic effects of the AAV rep gene products Expression of the rep gene products can be inactivated by, for example, replacing the first serine codon of Rep78/68 with an amber mutation thereby halting translation of the p5 message (Rep78*13). Likewise, expression of Rep 52/40 from the p19 promoter can be inactivated by placing an amber stop codon at position 14 (Rep52*14), the first serine codon of those proteins. Note, the open reading frames for all four rep proteins are identical at that site. Therefore, the rep52*14 stop codon inactivates expression of all four rep proteins.
Figure 2:
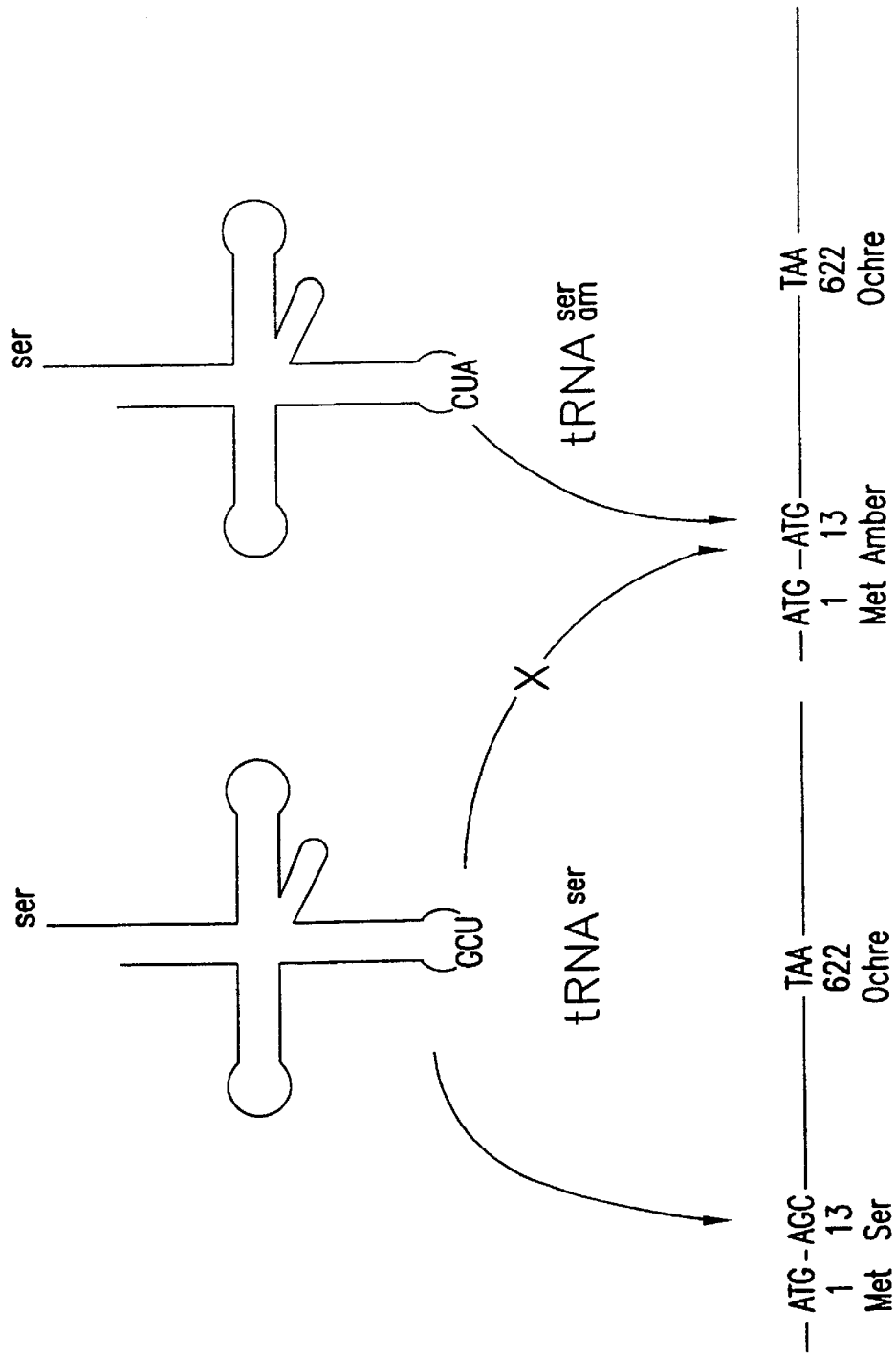
FIG. 2 Suppressor tRNA Translational arrest of rep protein synthesis can be bypassed by complementation with a termination codon suppressor tRNA. The structure of a human serine tRNA (left) and the amber suppressor tRNA (right) in which the GCU anticodon is replaced by a CUA anticodon are shown. The serine tRNA will insert a serine into the Rep78 protein at position 13 but will not recognize the thirteenth codon of Rep78*13 and therefore will not insert a serine into Rep78*13. The amber suppressor tRNA, on the other hand, will recognize the amber mutation in Rep78*13 and in turn will insert a serine into the growing polypeptide chain to make full-length Rep78. The amber suppressor should not have adverse effects on the normal ochre stop codon of rep78 and rep52 nor the opal stop codon of rep 68 and rep 40.

The instant invention relies on the strategic substitution of one or more termination codons in the coding sequence of a protein known to be toxic to a host cell. The protein toxic to the host cell may be but is not necessarily one that is foreign to the host cell. The toxic protein may be the desired gene product of interest or may be required for the expression of a desired gene product using recombinant nucleic acids. The introduced termination codon suppresses translation of the toxic protein and thus down regulates the expression and presence of the toxic protein in the host cell.

Then a specific complementing suppressor tRNA is used wherein the anticodon thereof recognizes the stop codon inserted into the coding sequence of the toxic protein of interest and the tRNA which is aminoacylated instead introduces an amino acid into the growing polypeptide. Therefore, the termination codon is overridden by the introduction of an amino acid at that site and translation proceeds resulting in production of the toxic protein.

The amino acid incorporated into the growing polypeptide at the site of the introduced termination codon can be that which would normally be found at the site which had been substituted by a termination codon. For example, if the seventh amino acid of a polypeptide is threonine and the seventh codon is replaced by a termination codon, a suitable complementing suppressor tRNA would be one which has an anticodon which recognizes the termination codon and which carries at the aminoacyl site, a threonine residue. However, it can be seen that the suppressor tRNA can carry any of a variety of amino acid residues at the aminoacyl site so long as translation occurs despite the presence of a termination codon and the function of the resulting polypeptide carrying an amino acid substitution at that site is maintained for the purposes intended without any deleterious effect.

The specific codon that is replaced by a termination codon can be selected at random in the coding sequence of the toxic protein of interest. Preferably the target codon which is to be replaced by a termination codon is located in the first half, preferably in the first third and more preferably in the first quarter of the growing polypeptide, that is, near the amino terminus. Thus, it is preferred the termination occurs at an earlier stage of translation rather than at a later stage.

The methods for introducing a termination codon into the coding sequence of the toxic protein are known in the art, for example, site-directed mutagenesis, targeted subcloning of a termination codon and so on.

Similarly, the construction of a suitable complementing suppressor tRNA is by methods known in the art. The minimum required for a suitable tRNA is an anticodon that recognizes the termination codon that was or is to be inserted into the coding sequence to bring about termination of translation and therefore minimizing expression of a cytotoxic proteins and that carries a suitable amino acid residue attached thereto at the aminoacyl site for incorporation into the growing polypeptide during translation. In that way, despite the presence of a termination codon, the suppressor tRNA will proceed to ensure incorporation of an amino acid during translation.

Because of the presence of release factors, termination factors and other factors associated with termination of translation in the host cell, it is necessary to provide the host cell with an adequate number of suppressor tRNA's to overcome the effect of those translation terminating factors on the termination codon(s) introduced into the coding sequence of the toxic protein encoding gene. That is to say, there must be an adequate amount of suppressor tRNA molecules in the cell so that it is more likely than not that a suppressor tRNA rather than the endogenous factors associated with termination will bind to the introduced termination codon. In fact, it is preferable that a large amount of tRNA molecules be present in the host cell to further enhance the likelihood that a suppressor tRNA rather than termination factors bind to the introduced termination codon so that expression of the toxic protein occurs.

The suppressor tRNA's also can be toxic to the host cell. Thus, it is preferable the presence of the tRNA's also be regulated or the suppressor tRNA's be introduced into the host cell just prior to the desired expression of the toxic protein of interest to minimize the exposure of the host cell to the suppressor tRNA's. Therefore, expression of a tRNA can be under the control of regulatory elements, such as a repressor element or an inducible promoter, or vectors carrying a tRNA coding sequence can be introduced into the host cell just prior to when expression of the target toxic protein of interest is desired. When producing recombinant AAV and expression of rep and/or cap proteins is regulated using the method provided herein, a suitable vector for carrying the tRNA coding sequence is an adenoviral vector because adenovirus provides necessary helper functions for the replication of AAV.

Any cell that can be used to produce recombinant gene products can be used in the practice of the instant invention. Therefore, prokaryotic and eukaryotic cells are contemplated to fall within the scope of the instant invention. Accordingly, bacterial cells, yeast cells, insect cells, mammalian cells and so on can serve as the host cell.

The suitably modified coding sequence that now contains a termination codon is introduced into a host cell practicing methods known in the art. Similarly, the coding sequence of the suppressor tRNA also is introduced into the host cell practicing methods known in the art. The result is regulated expression of the toxic protein that is the desired product of interest or is required to obtain the desired recombinant product of interest.

By regulating the expression of the suppressor tRNA's or by a directed exposure of the vector carrying the suppressor tRNA to the cells carrying the altered toxic protein gene that contains introduced termination codons just prior to use, it is possible to direct the expression of the desired protein of interest at a specific site or time in a host of interest.

The invention now having been described, reference is made to the specific examples noted hereinbelow which exemplify the invention of interest. One of the systems used to demonstrate the invention is the expression of recombinant AAV in mammalian cells. There are a number of different serotypes of AAV, such as serotypes I, II, III, IV and V, and expression of each is amenable in the practice of the instant invention. It should be recognized however, that the examples are mere exemplifications and in no way limit the invention of interest.

EXAMPLES

Methods

I. Construction of Plasmids and Viruses 1. pAdlox 12 sup tRNA

Figures 3A, 3B:
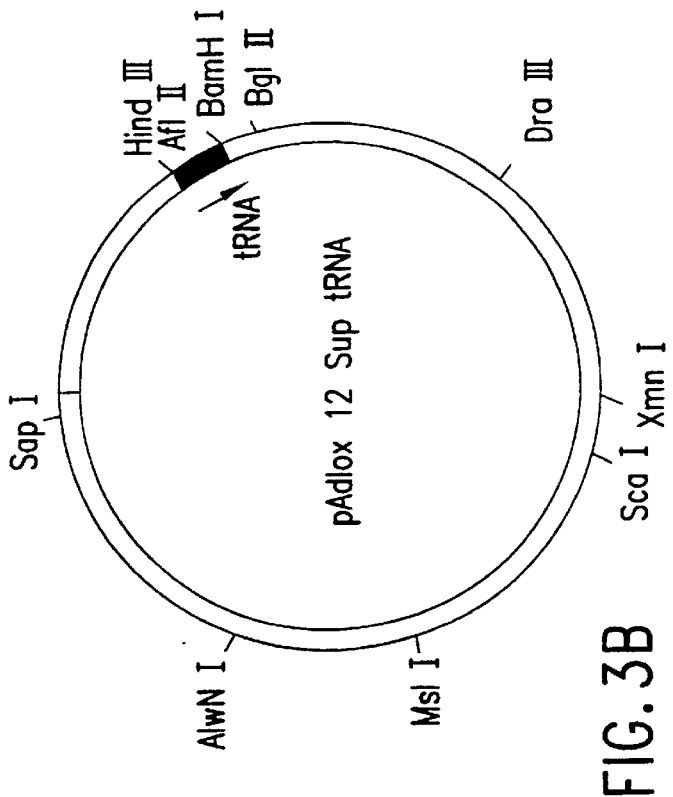
Figure 3C:
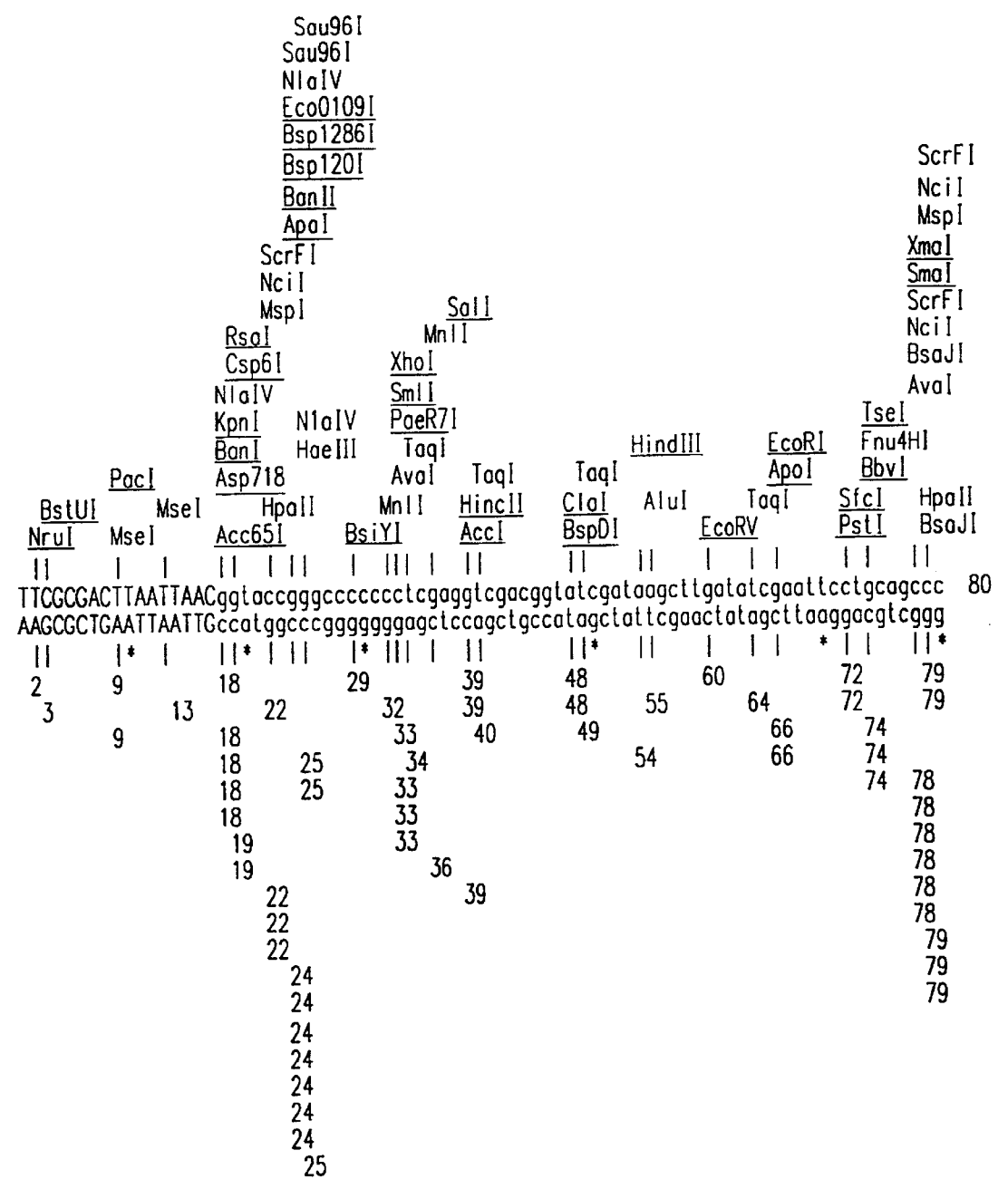

The amber suppressor tRNA gene was derived from a human serine tRNA gene (Capone et al., 1985) in which the serine anticodon was replaced with the amber anticodon (FIG. 3A). Linker regions containing the recognition sequences for HindIII, AflII and BamHI were situated on either side of the tRNA gene for cloning purposes. In addition, a 10-base spacer was inserted 3' to the tRNA gene. The spacer region enhances expression of RNA pol II transcribed genes (Geiducshek & Tocchini-Valentini, 1988).

The 116 bp DNA fragment containing the tRNA gene was generated by forming a scaffold with four oligonucleotide primers (shown in bold in FIG. 3A). Gaps in the scaffold were filled in by PCR using 10 cycles of 94° C. for one min, 55° C. for one min and 72° C. for one min. The 116 bp fragment then was amplified using primers 1 and 4 for 25 cycles under the same PCR conditions as above. DNA was purified from the PCR reaction mixture by extraction with phenol:chloroform followed by precipitation in ethanol. DNA pellets were resuspended in $H_2O$.

The PCR product was digested with BamHI and phosphorylated with T4 polynucleotide kinase. Plasmid pAdlox 12, which is essentially pAdlox (Hardy et al., 1997) in which the expression cassette was replaced by a polylinker, was digested with EcoRV and BamHI and then dephosphorylated with calf intestinal phosphatase. The two DNA's were ligated together with T4 DNA ligase to form plasmid pAdlox 12 sup tRNA (FIG. 3B). The identity of the plasmid was verified by DNA sequence analysis.

2. pUC-ACG pUC-ACG is an AAV helper plasmid used to supply AAV rep and cap functions. The pUC19.ACG construct contains the XbaI fragment of pACG2-1 described by Li et al. (1997) which was isolated by PCR. The 5' XbaI site was changed to a HindIII site and the 3' XbaI site was changed to a BamHI site. The fragment was inserted into the HindIII and BamHI sites in pUC19 and does not contain the adenoviral terminal repeats.

Figure 4:
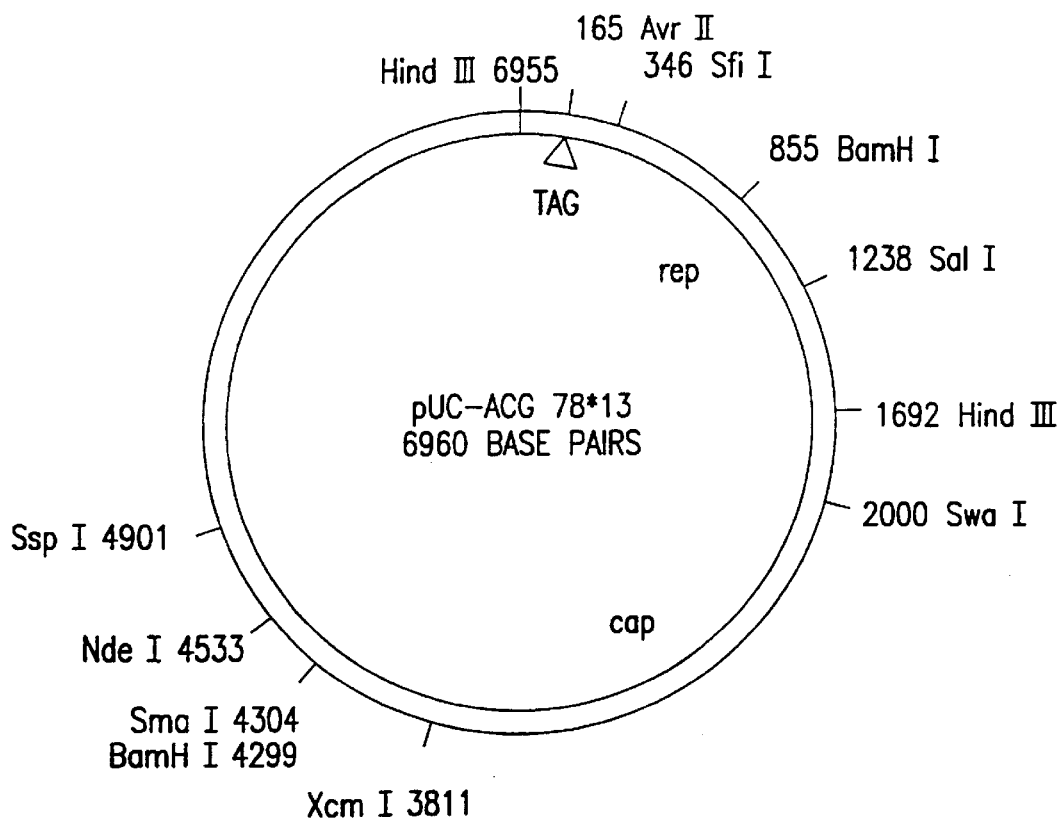
FIG. 4 Diagram of plasmid pUC-ACG 78*13 The TAG amber mutation in plasmid pUC-ACG 78*13 is identified by the AvrII site at position 165.

3. pUC-ACG 78*13 pUC-ACG 78*13 (FIG. 4) is an AAV helper plasmid in which the serine-encoding AGC codon at amino acid number 13 of the Rep78/68 proteins, AAV genome position 357 (GenBank accession no. AF 043303), was changed to a TAG amber stop codon. pUC-ACG 78*13 was generated by replacing the 187 bp PpuMI-SfiI fragment of pUC-ACG with a 187 bp PpuMI-SfiI fragment of pUC-ACG with a 187 bp PpuMI-SfiI fragment generated by PCR using the synthetic oligonucleotide primers, 5'-GATTAGGTCCCC <u>TAG</u>GACCTTGACGGGCATC-3' (SEQ IDNO: 1) and 5'-CCACGAGCACGTGCATGTGG-3' (SEQ ID NO:2), with pUC-ACG as the template, followed by digestion with PpuMI and SfiI. The amber codon is underlined.

4. pUC-ACG 78*13/52*14

Figure 5:
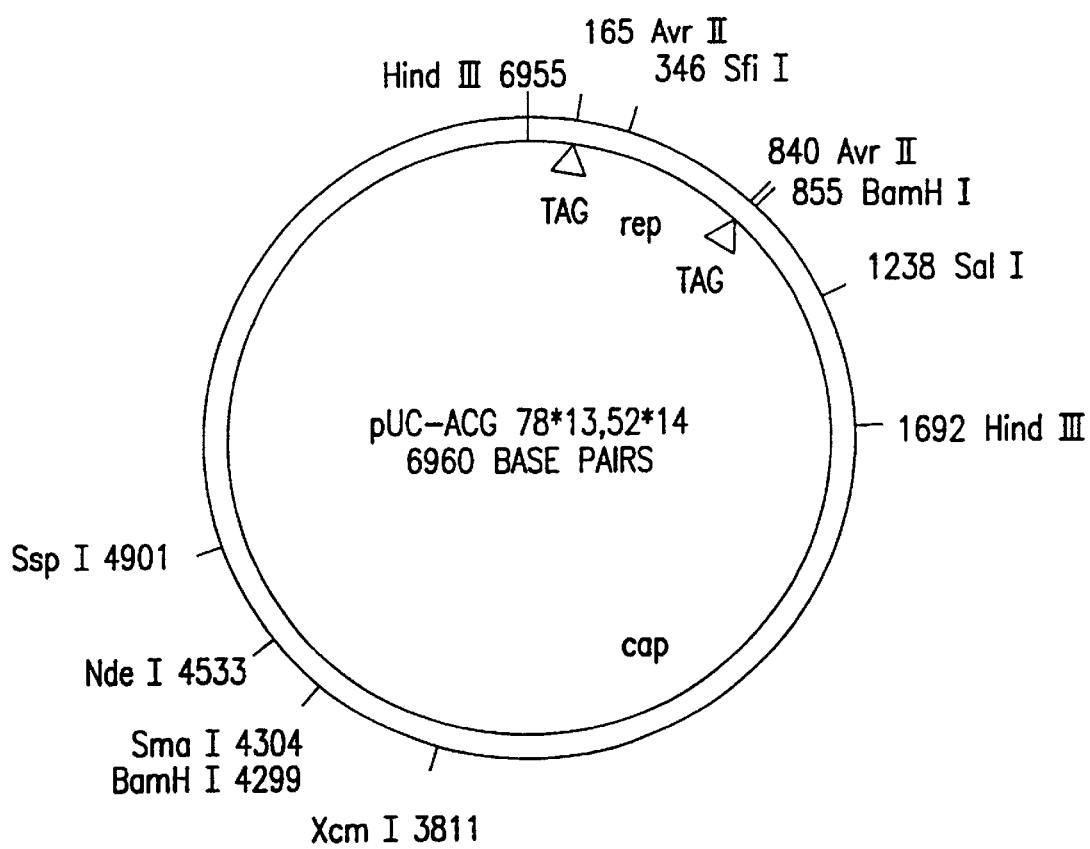
FIG. 5 Diagram of plasmid pUC-ACG 78*13, 52*14 The amber mutations at codon 13 of the rep78 gene and codon 14 of the rep52 gene are identified by the AvrII sites at positions 165 and 840, respectively.
Figure 6:
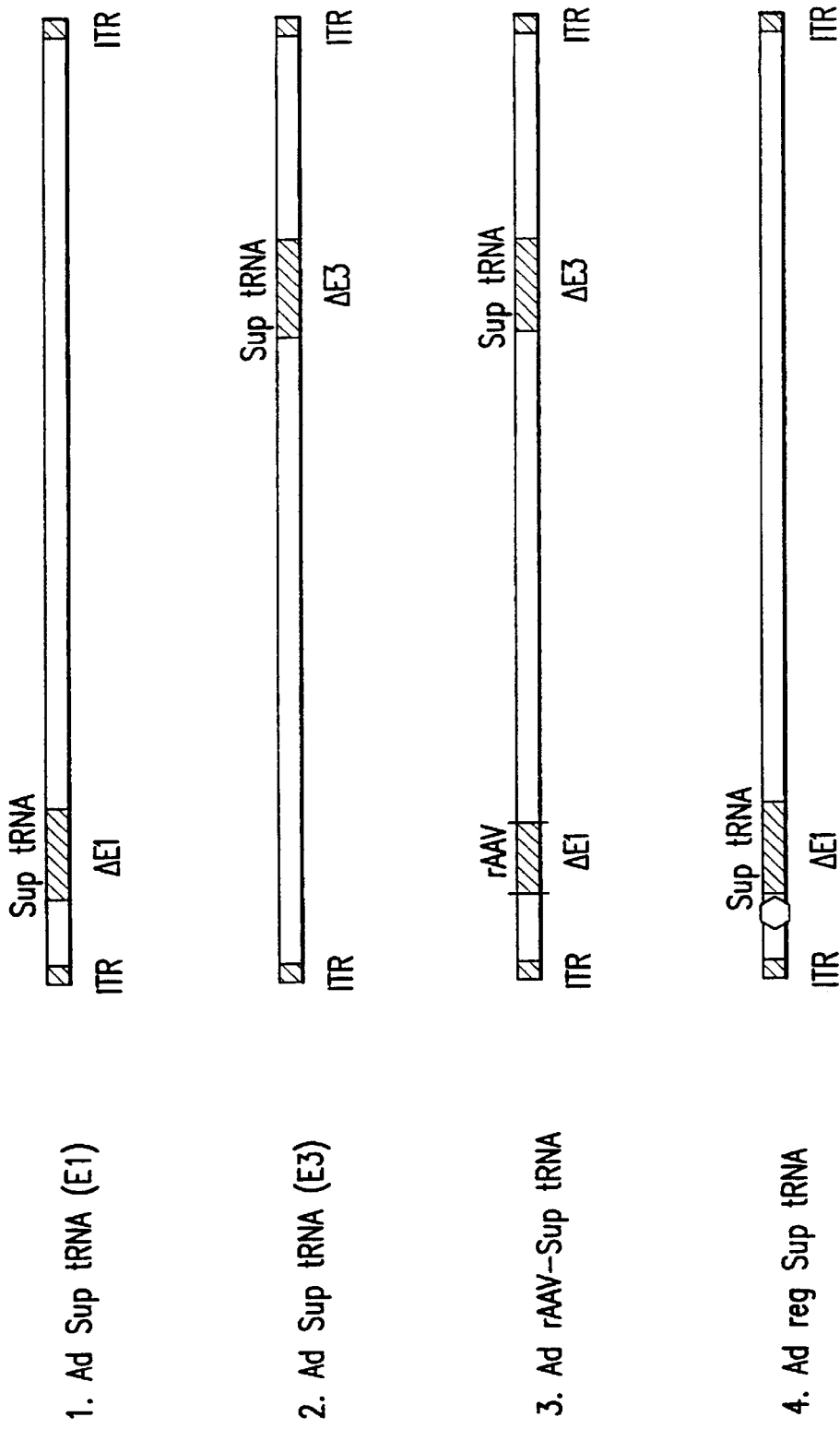
FIG. 6 Diagrams of Ad sup tRNA's An adenovirus encoding the suppressor tRNA gene can be located in either the E1 region or the E3 region. An adenovirus also can be made in which the amber suppressor tRNA gene is located in the E3 region and rAAV vector sequences are located in the E1 region. Conversely, the tRNA gene can be located in the E1 region and the rAAV sequences can be located in the E3 region. Adenovirus also can be constructed in which regulatory elements are included 5' to the tRNA gene.

In pUC-ACG 78*13/52*14 (FIG. 5), the TCG encoding the serine at amino acid number 14 of Rep 52, AAV genome position 1032 (GenBank accession no. AF 043303), was changed to a TAG amber stop codon. pUC-ACG 78*13/52*14 was generated by replacing the 362 bp SacII-BamHI fragment of pUC-ACG 78*13 with a 362 bp SacII-BamHI fragment generated by PCR using synthetic oligonucleotide primers, 5'-AGATTCGCGAAAAACTGAT-3' (SEQ ID NO:3) and 5'TCCTGGATCCACTGCTTCTC CTAGGTAATCCCCTTGTCCACGA3' (SEQ ID NO:4) with pUC-ACG as the template, followed by digestion with SacII and BamHI. The amber codon is underlined.

5. ptet EF GFP*3 ptet EF GFP*3 was made to serve as a control plasmid for the expression of the suppressor tRNA. The plasmid was made by introducing an amber stop codon at amino acid position 3 in the gene for green fluorescent protein (GFP). 293 cells were transfected with the plasmid using known techniques, such as by using calcium phosphate. Five hours after transfection, the cells were infected with either Ad5 dl312, an E1A$^-$ mutant) at a multiplicity of infection (m.o.i.) or 2, or with Ad5 sup tRNA at an m.o.i. of 2 or 5. Cells receiving the GFP*3 plasmid were examined under a fluorescence microscope 66 hours after infection. Approximately 30% of the cells expressed GFP. That indicated that both the plasmid delivered GFP gene and the viral delivered suppressor tRNA were expressed in the 293 cells.

6. Ad sup tRNA

Adenovirus encoding the human amber suppressor tRNA was prepared from plasmid pAdlox 12 sup tRNA as described by Hardy et al. (1997). The suppressor tRNA gene was placed in the E1 region of adenovirus although the tRNA gene could also be placed in the E3 region. In addition, the tRNA gene can be placed in the E3 region and rAAV vector sequences can be placed in the E1 region to enable synthesis of rAAV without the need for transient transfection of the rAAV vector.

7. rAd-rAAV-CMV-lacZ rAd-rAAV-CMV-lacZ was constructed by removing a fragment containing the AAV ITR's and the lacZ gene from plasmid pdx11 lacZ (McCown et al., 1996) and inserting that fragment into the SmaI site of pAdlox 12. The resulting plasmid was used to prepare adenovirus in which the lacZ gene was flanked by the AAV ITR's.

8. pRT43.267 pRT43.267 is a variant of rkat3 in which the MMLV Psi sequences (up to Gag ATG, which had been mutated to TAG) were replaced with corresponding MMSV sequences (Finer et al., 1994). Viral env coding sequences between the cloning site and the reverse-strand primer binding site were deleted. Inserts can be cloned into the polycloning site (5'-EcoRI-ApaI 3').

9. pTRorf6*17

The amber* 17 mutation was introduced into the E4 gene of Adenovirus type5 (Ad5) by PCR, in which two oligonucleotides, orf6*17 (5'CCATTTGGCATGACAC-TACGACCAACACGA$\underline{TAG}$CGGTTGTCTCGGCGCACT-CC 3') (SEQ ID NO:5) and orf6 3' (5'GCTCCGG-TCGACTCACATGGGGTAGAGTCATAATC3') (SEQ ID NO:6) were used as primers. To generate the full Ad E4orf6 gene, the above PCR products were added to a second PCR reaction using primers orf6 5' (5'CCCGGAT-CCAAATATGACTACGTCCGGCGTTCCATTTGGCAT-GACACTAC3') (SEQ ID NO:7) and orf6 3'. Subsequently, the E4 orf6*17 fragment was inserted into the unique EcoRI site of the pRT43.267 plasmid. The final plasmid construct contains Moloney retroviral 5'LTR and packaging sequences; half of the gag sequence; E4orf6*17; and the Moloney retroviral 3' LTR. The E4orf6*17 plasmid was sequenced to verify the accuracy of the sequence.

10. Ψ17

Ψ17 is a $^\Delta$E1/$^\Delta$E4 adenovirus vector with a humanized CMV promoter and a green fluorescent protein (GFP) gene (Clontech) in the E1 region. The genotype is $^\Delta$E1a, $^\Delta$E1b (deletion of nucleotides 454 to 3328) and $^\Delta$E4 (H5dl 1014 deletion=orf 1$^-$, 2$^-$3$^-$, 6$^-$, 6/7$^-$ and orf 4$^+$). The vector is described in Bridge & Ketner, 1990.

11. pUC-sup pUC-sup is a plasmid encoding the suppressor amber tRNA$^{ser}$ and containing no adenoviral sequences. PUC-sup was generated from plasmids pAdlox12-suptRNA and pUC19-ACG. PAdlox12-suptRNA was digested with HindIII and BamHI and a 110 bp fragment containing the suppressor tRNA was isolated. Plasmid pUC19-ACG was digested with HindIII, BamHI and NcoI and a 2656 bp fragment containing the pUC19 vector backbone was isolated. The 110 bp and 2656 bp fragments were ligated to form pUC-sup.

II. Production of rAAV-CMV-LacZ Using the sup tRNA System 1. pUC-ACG 78*13 rAAV encoding the LacZ gene (rAAV-CMV-LacZ) was prepared as described (Snyder et al., 1996) with minor modifications. Briefly, human 293 cells were co-transfected with the vector plasmid, pdx 11 LacZ (McCown et al., 1996) and either the helper plasmid, pUC-ACG, or the mutated helper plasmids, pUC-ACG 78*13 or pUC-ACG*13*14, using the calcium phosphate method.

Cells from all samples were harvested and lysed by three rounds of freeze/thaw. The functional titers of rAAV-CMV-LacZ in each sample were determined by infecting 293 cells with limiting dilutions of the cell lysates. After 24 hours incubation, cells were stained with X-gal and β-galactosidase positive cells were counted.

Figure 7:
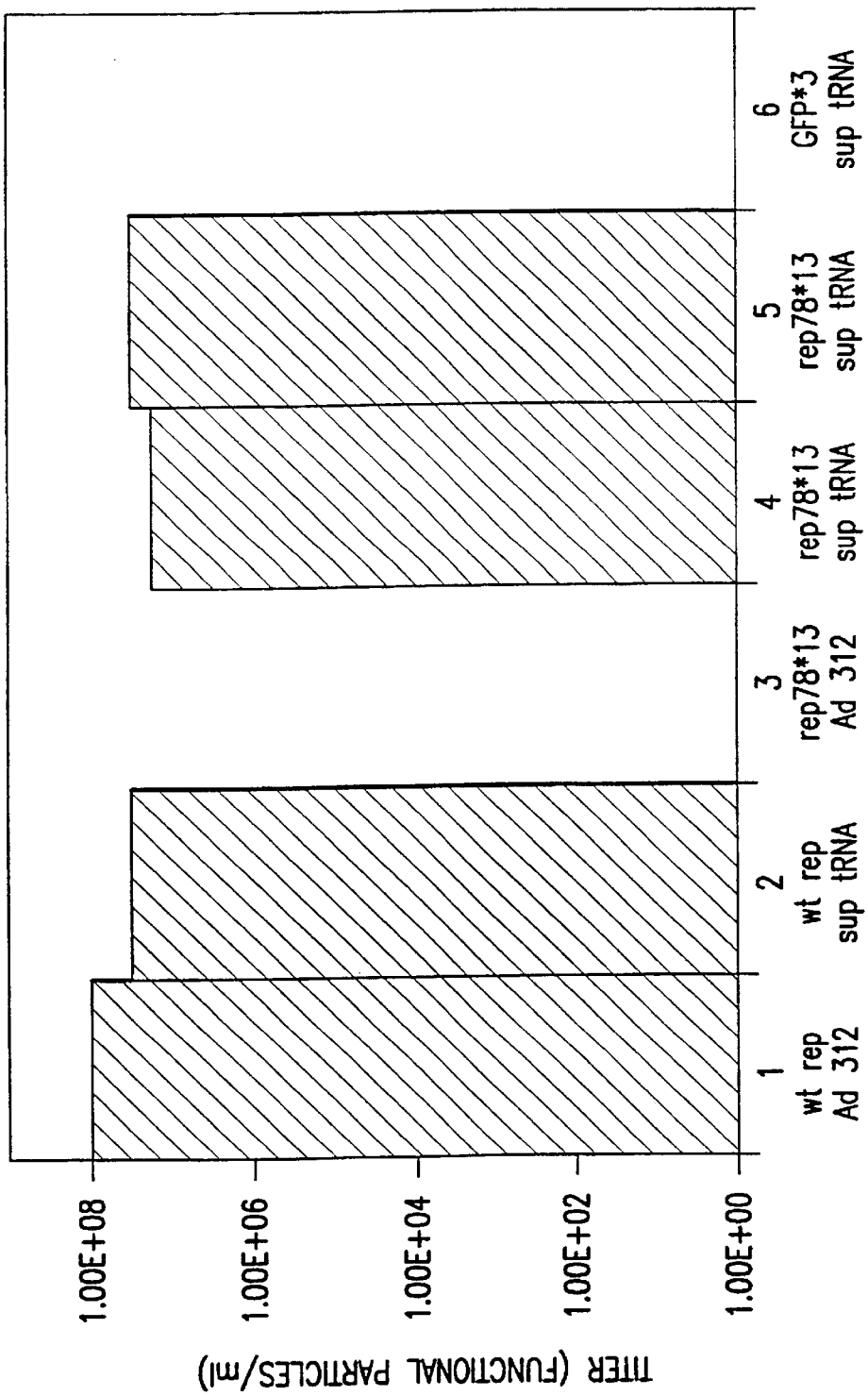
FIG. 7 Production of rAAV-CMV-LacZ using the rep78*13/sup tRNA system Human 293 cells were transfected with either pUC-ACG (columns 1 and 2) or with pUC-ACG rep 78*13 (columns 3–5). Five hours later, cells were infected with either Ad5 dl312 at an MOI of 2 (columns 1 and 3) or with Ad5 sup tRNA at an estimated MOI of 2 (columns 2 and 4) or 10 (column 5). As a control to monitor sup tRNA expression, cells were infected with a plasmid expressing a GFP gene containing an amber mutation at codon 3 and then infected with Ad5 sup tRNA at an MOI of 2 (column 6). Cells were harvested and lysed after incubation for three days. Cell lysates then were assayed for rAAV by transduction of 293 cells. Results are shown as the titer in functional particles/ml.

Results of the functional assay are presented in FIG. 7. Titers of rAAV-CMV-LacZ from cells transfected with pUC-ACG and infected with Ad dl312 or Ad sup tRNA were $1.2 \times 10^8$ and $2.8 \times 10^7$, respectively. No titer was detected from cells transfected with pUC-ACG 78*13 and infected with Ad dl312. The limit of detection of the assay was determined to be $1 \times 10^4$ suggesting that there was at least a three-log drop in titer due to the presence of the amber mutation in rep78. Titers obtained from cells receiving pUC-ACG 78*13 and Ad sup tRNA were $1.6 \times 10^7$ and $3.4 \times 10^7$. The values are similar to the titers obtained from pUC-ACG indicating that the amber mutation in the rep gene was suppressed sufficiently to produce normal titers of rAAV.

Up to 60% suppression of an amber mutation in the GFP gene was obtained. If similar levels of suppression are obtained for the rep gene, then suppression of the amber mutation in the rep gene results in normal levels of rAAV production and expression of rep is not the limiting factor in the production of rAAV. Indeed, expression of the cap gene was found to be limiting for production of rAAV. Moreover, high expression of rep from a strong promoter has been shown to decrease the yield of rAAV (Li et al., 1997).

2. pUC-ACG 78*13,52*14

Figure 8:
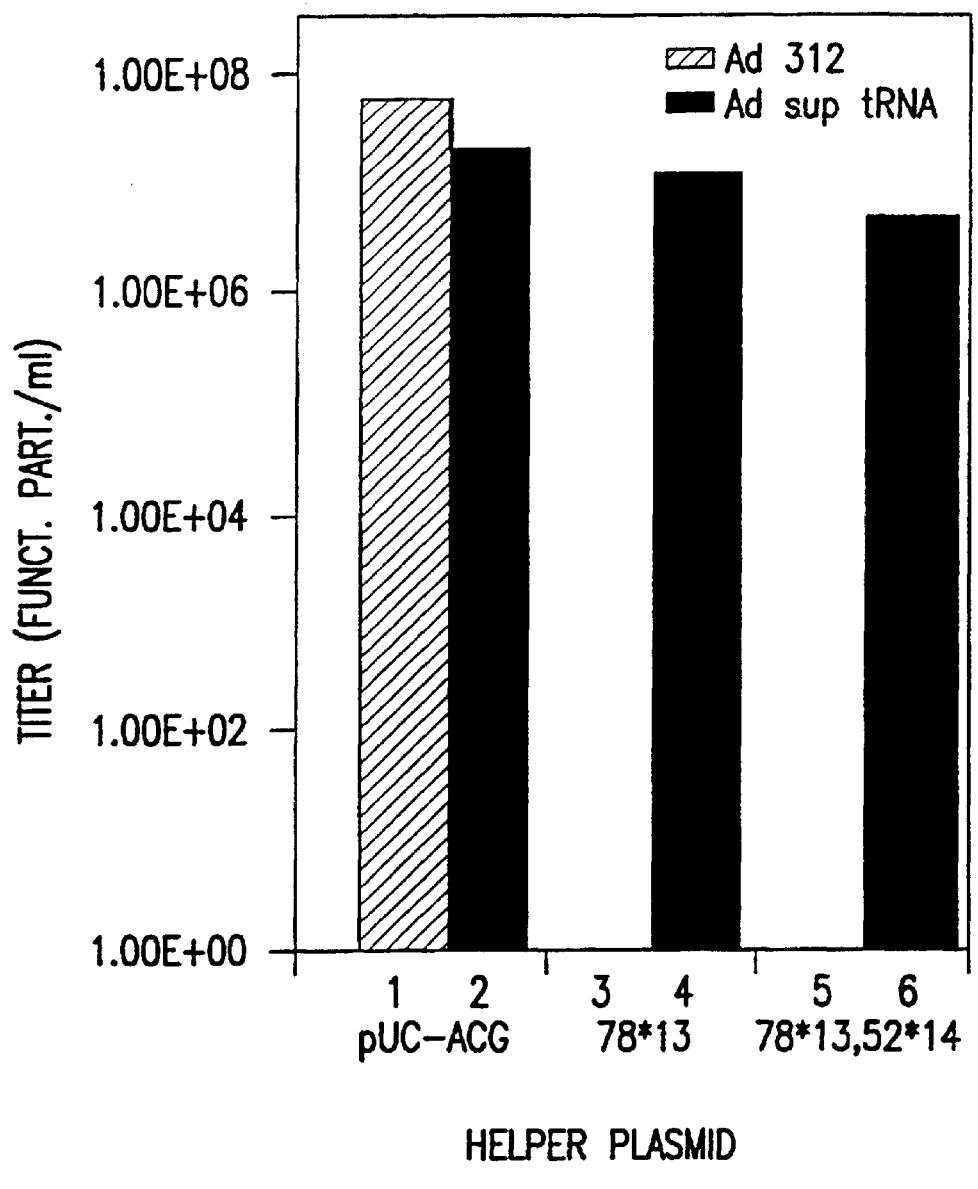
FIG. 8 Production of rAAV-CMV-LacZ using the rep78*13,52*14 Human 293 cells were transfected with either pUC-ACG (columns 1 and 2), pUC-ACG 78*13 (columns 3 and 4) or pUC-ACG 78*13,52*14 (columns 5 and 6). Five hours later, cells were infected with either Ad5 dl312 at an MOI of 2 (columns 1, 3 and 5) or with Ad5 sup tRNA at an estimated MOI of 2 (columns 2, 4 and 6). Cells were harvested and lysed after incubation for three days. Cell lysates then were assayed for rAAV by transduction of 293 cells. Results are shown as the titer in functional particles/ml.

The Ad sup tRNA can suppress two amber mutations in the AAV helper plasmid. Plasmid pUC-ACG 78*13,52*14 contains amber mutations at the first serine codon downstream of the Rep78 start codon, AAV genome position 357 and at the first serine codon downstream of the Rep52 start codon, AAV genome position 1032. Recombinant AAV was prepared as described above and the functional titers of rAAV-CMV-LacZ in crude lysates were tested by transduction of 293 cells (FIG. 8). Similar titers were obtained from samples in which the helper plasmid was either pUC-ACG, pUC-ACG 78*13 or pUC-ACG 78*13,52*14 followed by infection with Ad sup tRNA (columns 2, 4 and 6). In cases were the cells were infected with Ad dl312, however, rAAV was produced only with the parental pUC-ACG plasmid (column 1). No virus was produced using either the single amber mutation (column 3) or the double amber mutation (column 5). The results demonstrate the suppressor tRNA delivered by an adenovirus can suppress effectively two amber mutations to produce rAAV.

3. pUC-ACG 78*13 and vTR LacZ

The efficacy of delivering the vector plasmid carried on an adenovirus was investigated. 293 cells were transfected with plasmid pUC-ACG 78*13. Cells then were infected with Ad vTR-LacZ, an adenovirus encoding the LacZ gene flanked by the AAV ITR's. rAAV-CMV-LacZ can be prepared from cells infected with that virus. Cells were coinfected with either Ad dl312 (FIG. 9, columns 1 and 2) or Ad sup tRNA (columns 3 and 4). Infected cells were incubated for three days and lysates were prepared by multiple freeze-thaw cycles. A portion of each sample was heated to inactivate the Ad vTR LacZ present in the lysates thereby measuring only rAAV-CMV-lacZ because it is heat stable.

Figure 9:
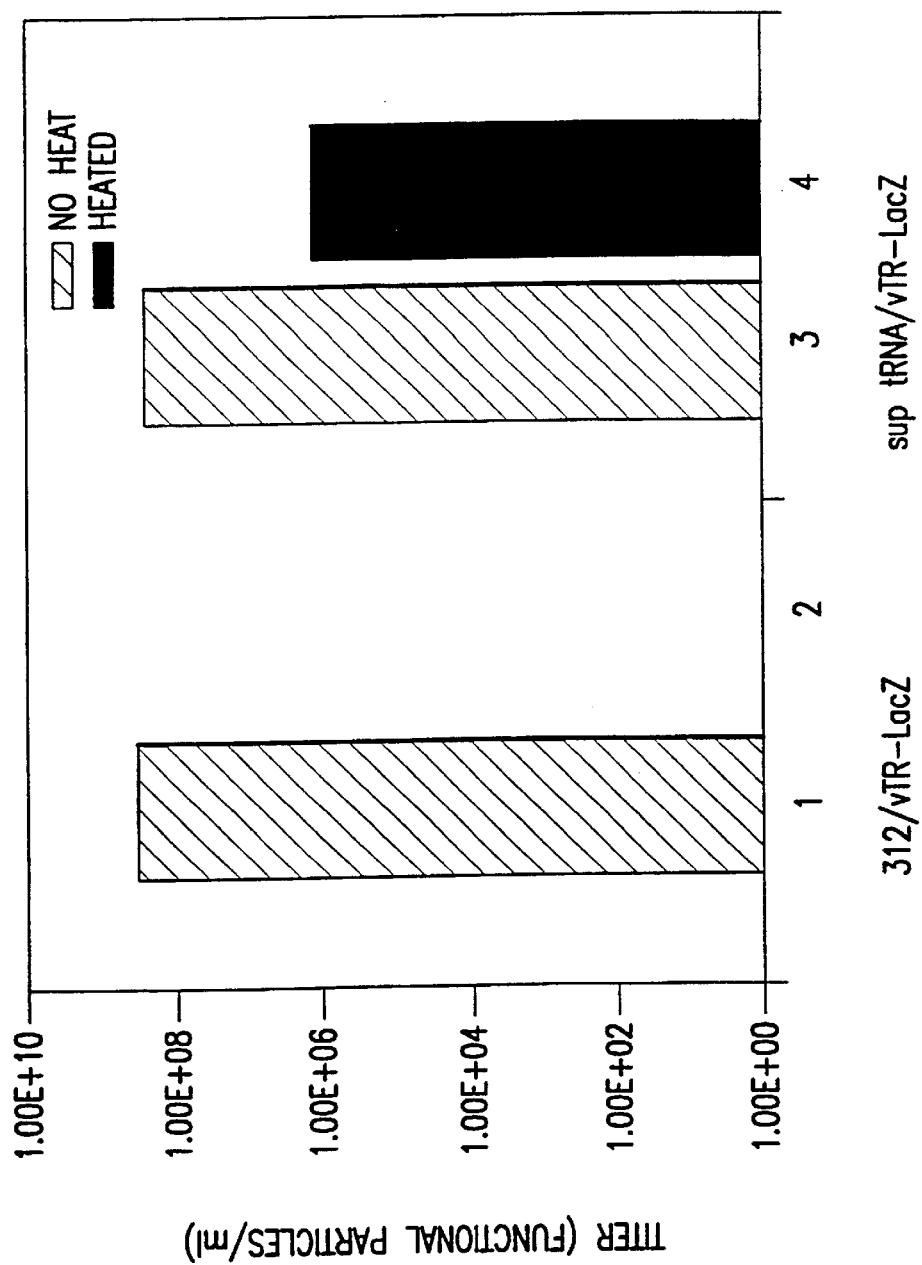
FIG. 9 Production of rAAV-CMV-LacZ using the rep78*13/sup tRNA system and an AAV/adenovirus hybrid 293 cells were transfected with pUC-ACG 78*13 and then coinfected with Ad vTR-LacZ and Ad dl312 (columns 1 and 2) or with Ad vTR-LacZ and Ad sup tRNA (columns 3 and 4). After three days, cell lysates were prepared and a portion of each lysate was heated to inactivate adenovirus. Both nonheated (columns 1 and 3) and heated (columns 2 and 4) samples were assayed for rAAV by transduction. Results are presented as the titer in functional particles/ml.
Figure 10:
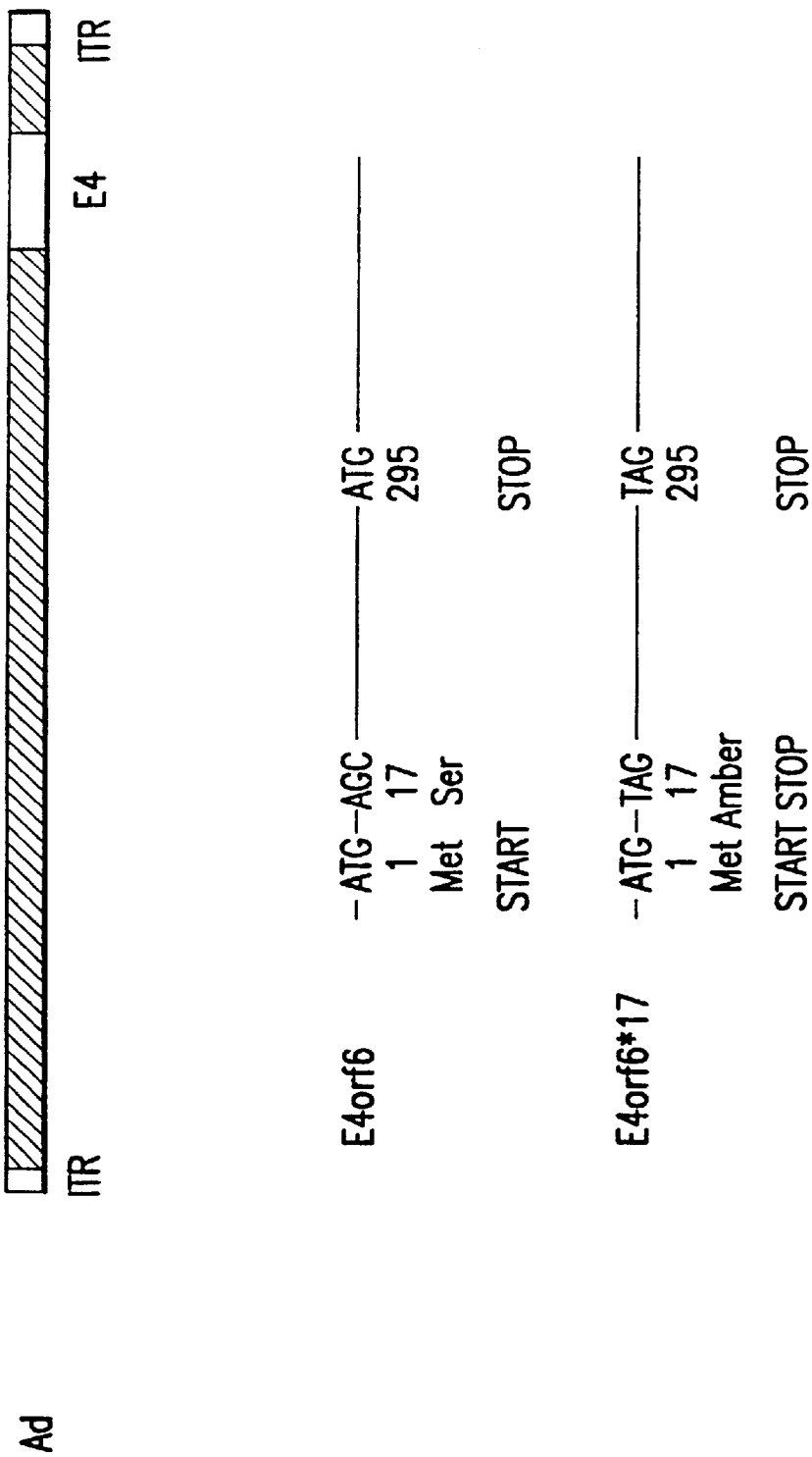
FIG. 10 Scheme for minimizing the toxic effects of E4 for the production of adenovirus Expression of E4 can be controlled, for example, by manipulating a serine codon and using an amber mutation to disrupt translation.
Figure 11:
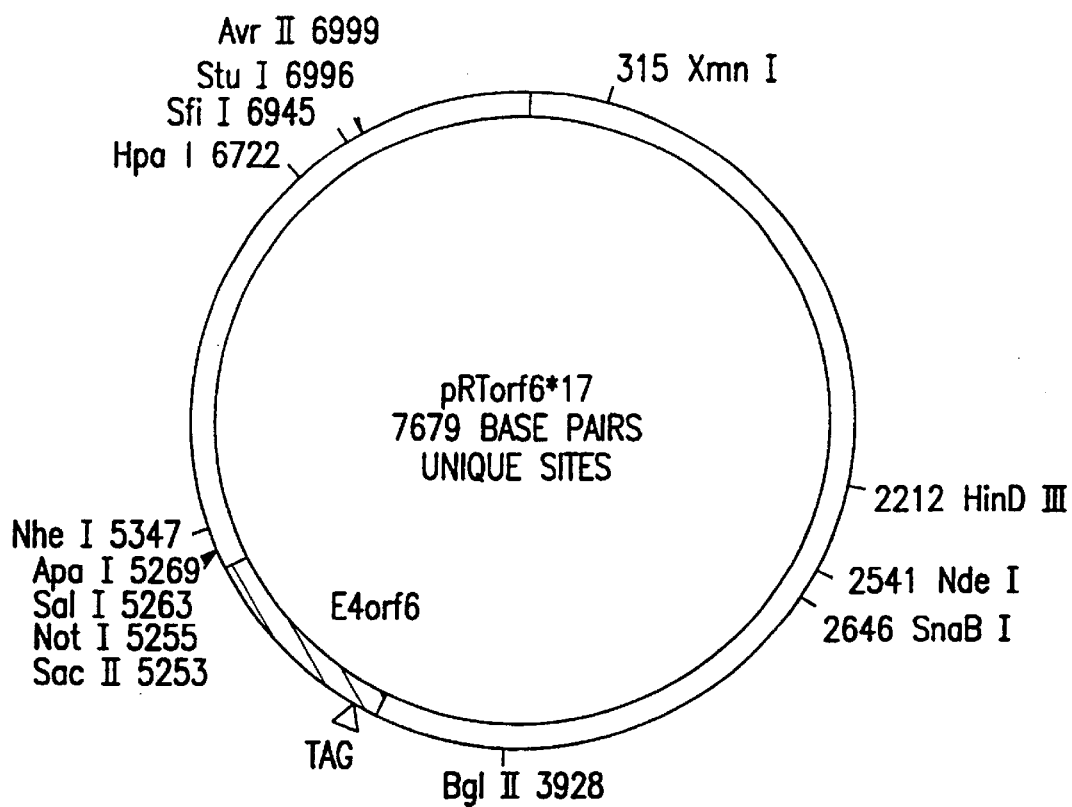
FIG. 11 Diagram of plasmid pRTorf6*17 The TAG amber mutation is highlighted.
Figure 12:
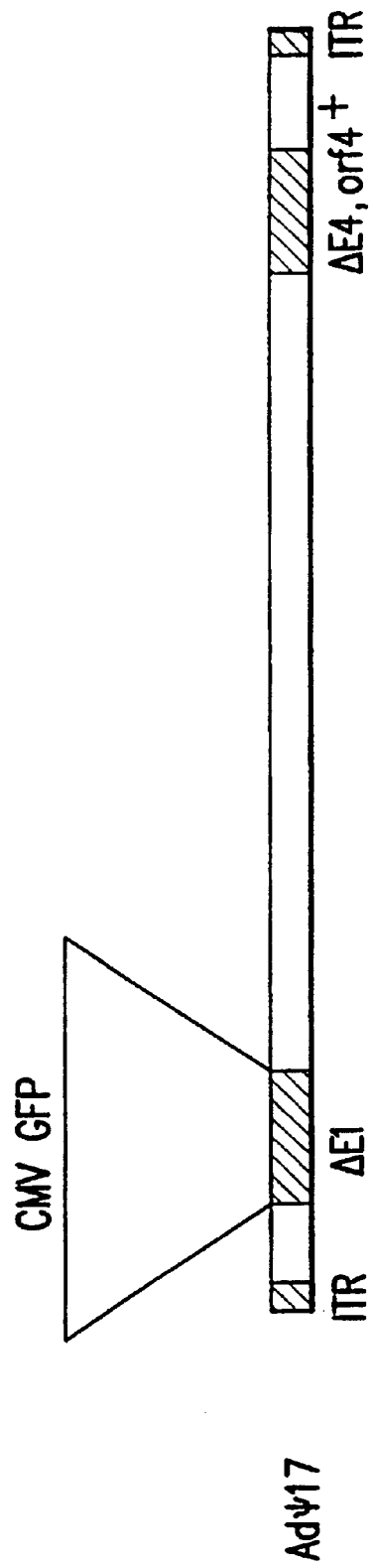
FIG. 12 Diagram of Ad ψ17 ITR is an inverted terminal repeat. CMV is the cytomegalovirus promoter. GFP is green fluorescent protein.
Figure 13:
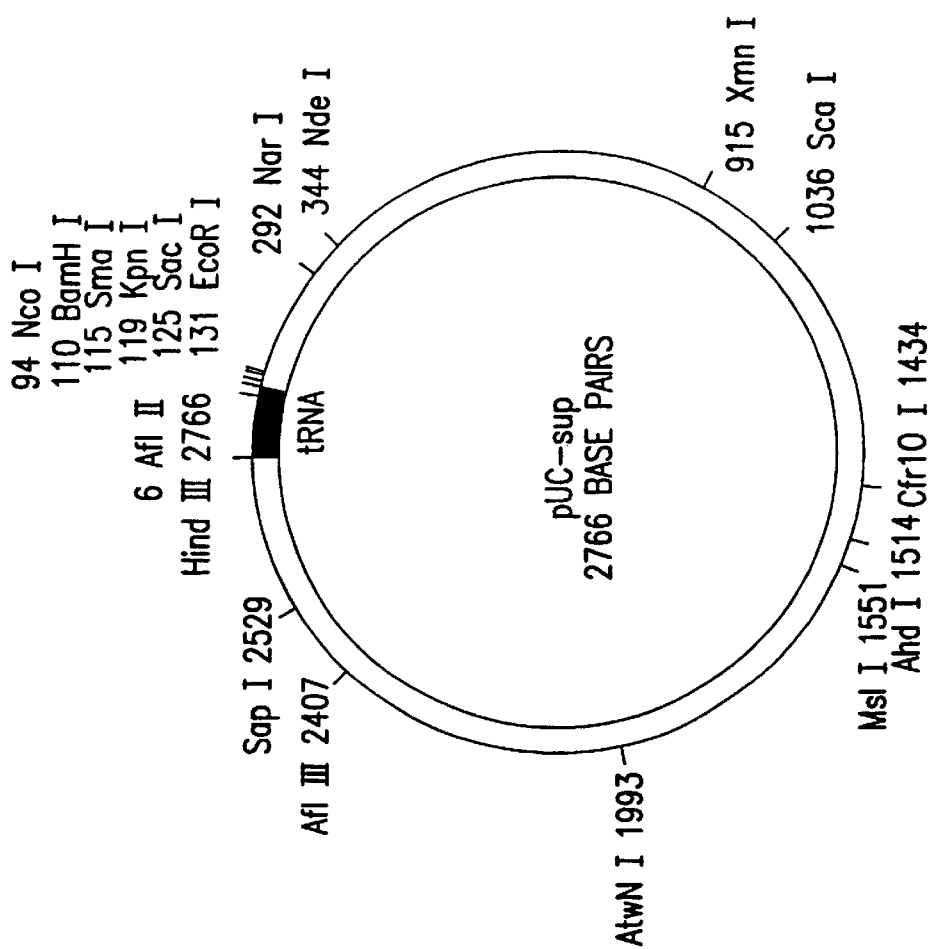
FIG. 13 Diagram of pUC-sup Vector containing an amber mutation in a serine codon but containing no adenoviral sequences.

As seen in FIG. 9, the titers of the adenovirus in the nonheated lysates were approximately $3 \times 10^8$ functional units/ml (columns 1 and 3). No rAAV was detected from cells infected with Ad dl312 (column 2) whereas cells receiving Ad sup tRNA yielded heat-stable rAAV titers of $1 \times 10^6$ functional units/ml (column 4). The results indicate that rAAV can be produced by coinfection of an adenovirus encoding the rAAV vector sequence and an adenovirus encoding the suppressor tRNA gene. That should prove useful for screening clones of rAAV producer cells in which the rep78*13 or rep78*13,52*14 gene is integrated into the host chromosome in stable producer cell lines.

III. Production of Adenovirus

The adenovirus E4 gene is required for adenovirus growth. Recombinant adenoviral vectors can be constructed which lack the E4 region but those vectors require transcomplementation with E4. Cell lines that express the E4 proteins are difficult to produce because of the toxic nature of the E4 proteins. Thus, tight control of E4orf6 gene expression is important for generating stable cell lines which can express E4orf6 for the production of recombinant adenoviral vectors lacking those sequences.

Stable 293orf6*17 cell lines were made by growing 293 cells (ATCC CRL 1573) in DMEM with high glucose and 10% calf serum. The cells were seeded at $6 \times 10^6$ per 10 cm plate 6 hours before transfection. Then 10 μg of pRTorf6*17 and 1 μg or pPUR (CLONTECH, encoding the puromycin resistance gene under the control of the SV40 promoter), were cotransfected into the 293 cells by calcium phosphate precipitation. The cells were refed with normal medium after 16 hours. About 48 hours after transfection, the medium was changed to selective medium containing 1 μg/ml puromycin (Sigma). The cells were refed with fresh selective medium every 3 days for about 2–3 weeks. Twelve clones were isolated and expanded for further characterization.

293orf6*17 and 293 (as a control) cell lines were plated in 6 cm plates at $2.5 \times 10^6$ cells per plate 6 hours before transfection. Then, 3 μg of pAdlox suptRNA were introduced into the cells by calcium phosphate precipitation. About 24 hours after transfection, all plates were infected with $\Psi 17$ at a MOI=1 (2 μl of $\Psi 17$ lysate at $1.25 \times 10^9$ pfu/ml). Pour days after infection, cells were harvested from all plates. After 3 rounds of freezing and thawing, 100 μl of the lysate were used to transduce $3 \times 10^6$ 293 cells. After 4 days, the cells were harvested for a second passage onto 293 cells. Positive cells infected with adenovirus were counted to determine the viral titers generated.

Figure 14:
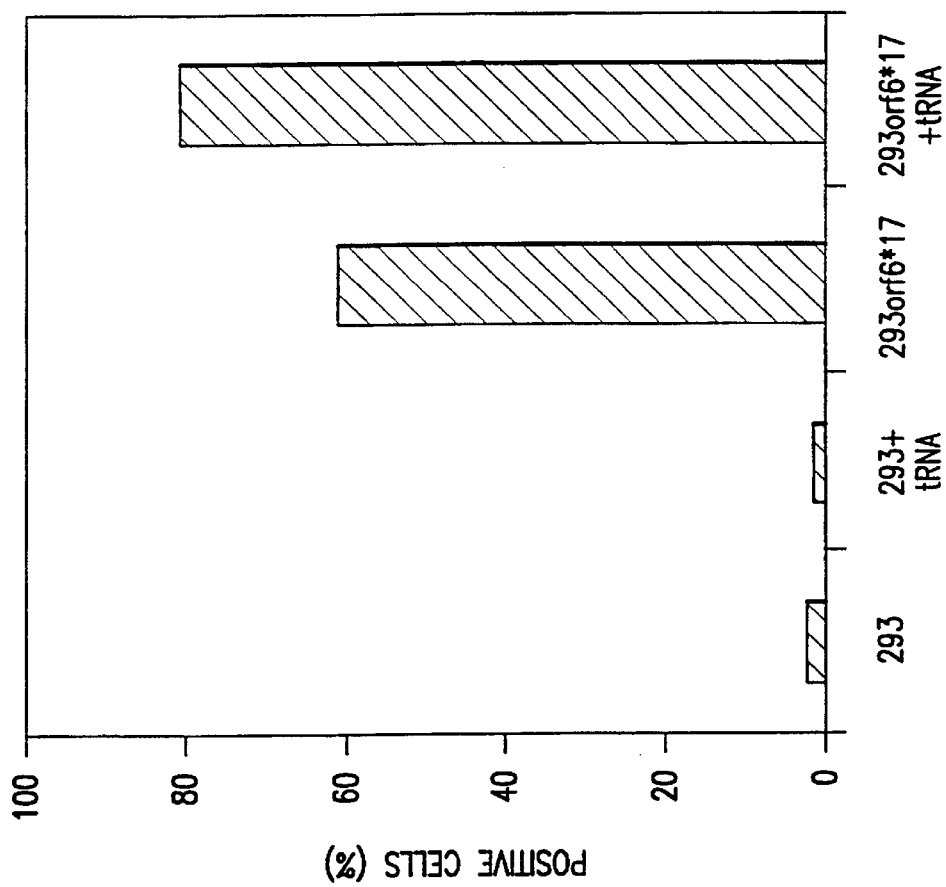
FIG. 14 Production of Adenovirus Stable cells expressing E4 were transfected with a sup tRNA vector and an adenovirus vector to determine the expression of adenovirus by those cells. The levels of positive cells represents the number of cells infected with virus and is indicative of ψ17 virus titer produced by the transfected cells. 293 cells (columns 1 and 2) and 293orf6*17 cells (columns 3 and 4) were transfected with pAdlox sup tRNA (columns 2 and 4) and infected with ψ17.

As seen in FIG. 14, 293 cells that do not express E4 do not yield $\Psi 17$ virus. However, the stable E4 producing cells complement the $\Psi 17$ vector to yield $\Psi 17$ virus.

REFERENCES

Bridge, E. & G. Ketner (1990) Interaction of adenoviral E4 and E1b products in late gene expression. Virology 174 (2): 345–353.

Capone, J. P., P. A. Sharp & U. L. RajBhandary (1985) Amber, ochre and opal suppressor tRNA genes derived from a human serine tRNA gene. EMBO J. 4:213–221.

Chejanovsky, N. & B. J. Carter (1989) Replication of a human parvovirus nonsense mutant in mammalian cells containing an inducible amber suppressor. Virology 171:239–247.

Drabkin, H. J., H.-J. Park & U. L. RajBhandary (1996) Amber suppression in mammalian genes dependent upon expression of an Escherichia coli aminoacyl-tRNA synthetase gene. Mol. Cell. Biol. 16:907–913.

Geiducshek, E. P. & G. P. Tocchini-Valentini (1988) Transcription by RNA polymerase III. Ann. Rev. Biochem. 57:873–914.

Finer, M. H., T. J. Dull, L. Qin, D. Farson & M. R. Roberts (1994) kat: a high-efficiency retroviral transduction system for primary human T lymphocytes. Blood 83:43–50.

Hardy, S., M. Kitamura, T. Harris-Stansil, Y. Dai & M. L. Phipps (1997) Construction of adenovirus vectors through Cre-lox recombination. J. Virol. 71:1842–1849.

Kyostio, S., S. Piraino, K. Vincent & S. C. Wadsworth (1997) Adeno-associated (AAV) recombinant vectors-comprise DNA encoding AAV rep protein and DNA encoding protein of interest flanked by two AAV inverted terminal repeat sequences. WO97/09441.

Li, J., R. J. Samulski & X. Xiao (1997) Role for highly regulated rep gene expression in adeno-associated virus vector production. J. Virol. 71:5236–5243.

McCown, T. J., X. Xiao, J. Li, G. R. Breese & R. J. Samulski (1996) Differential and persistent expression patterns of CNS gene transfer by an adeno-associated virus (AAV) vector. Brain Res. 713:99–107.

Park, H.-J. & U. L. RajBhandary (1998) Tetracycline-regulated suppression of amber codons in mammalian cells. Mol. Cell. Biol. 18:4418–4425.

Snyder, R. O., X. Xiao & R. J. Samulski (1996) Production of recombinant adenoassociated viral vectors. In "Current Protocols in Human Genetics", N. Dracopoli, J. Haines, B. Krof, D. Moir, C. Morton, C. Seidman, J. Seidman and D. Smith, eds. Gohn Wiley and Sons, New York) pp.12.1.1–24.

Vincent, K. A., S. T. Piraino & S. C. Wadsworth (1997) Analysis of recombinant adeno-associated virus packaging and requirements for rep and cap gene products. J. Virol. 71:1897–1905.

All references cited are herein and incorporated by reference.

The invention now having been described and exemplified, it will be evident to one of ordinary skill in the art that various changes and modifications can be made thereto without departing from the spirit and scope of the instant invention.

We claim:

1. A method for producing adenovirus, comprising:
   (a) producing a host cell which expresses a gene product or where expression of said gene product requires an accessory protein, wherein said gene product, said accessory protein or both are required for adenovirus production and are toxic to said cell, by introducing a termination codon into a nucleic acid encoding said gene product or a nucleic acid encoding said accessory protein in said cell to down regulate production of said gene product or said accessory protein;
   (b) introducing into said host cell, adenovirus packaging plasmids for expressing components of adenovirus particles;
   (c) expressing a tRNA in said cell, wherein said tRNA comprises an anticodon for said introduced termination codon and an amino acid for incorporation into a polypeptide during translation to suppress said introduced termination codon; and
   (d) retrieving adenovirus produced by said host cell.

2. The method of claim 1 wherein said gene product is E4.

3. A method for regulating expression of adeno-associated virus (AAV) REP or CAP in a cell, comprising:
   (a) introducing a termination codon into a nucleic acid encoding REP or CAP;
   (b) introducing said nucleic acid into said cell;
   (c) transforming said cell with a recombinant viral vector that provides helper functions for replication of AAV, said viral vector carrying a tRNA, wherein said tRNA comprises an anticodon for said introduced termination codon and an amino acid for incorporation into REP or CAP during translation to suppress said introduced termination codon; and
   (d) expressing said REP or CAP in said cell, wherein said REP or CAP contains said amino acid at the site corresponding to the location of said introduced termination codon.

4. The method of claim 3, wherein said termination codon is an amber codon, an opal codon or an ochre codon.

5. The method of claim 3, wherein said termination codon is introduced in the first half of the nucleic acid encoding REP or CAP.

6. The method of claim 3, wherein said introduced termination codon replaces a serine codon.

7. The method of claim 3, wherein said viral vector is an adenoviral vector.

8. A method for regulating expression of adeno-associated virus (AAV) REP or CAP in a cell, comprising:
   (a) introducing a termination codon into a nucleic acid encoding REP or CAP;
   (b) introducing said nucleic acid into said cell;
   (c) transforming said cell with a recombinant adenoviral vector that provides helper functions for replication of AAV, said adenoviral vector carrying a tRNA, wherein said tRNA comprises an anticodon for said introduced termination codon and an amino acid for incorporation into REP or CAP during translation to suppress said introduced termination codon; and (d) expressing said REP or CAP in said cell, wherein the said REP or CAP contains said amino acid at the site corresponding to the location of the said introduced termination codon.

9. The method of claim 8, wherein said termination codon is an amber codon, an opal codon or an ochre codon.

10. The method of claim 8, wherein said termination codon is introduced in the first half of the nucleic acid encoding REP or CAP.

11. The method of claim 8, wherein said introduced termination codon replaces a serine codon.

12. A kit, comprising;
   (a) a cell comprising a nucleic acid encoding adeno-associated virus (AAV) REP or CAP, wherein said nucleic acid comprises an introduced termination codon; and
   (b) a recombinant adenovirus comprising a nucleic acid encoding a tRNA for transiently transforming said cell, wherein said tRNA comprises an anticodon for said introduced termination codon and an amino acid at the aminoacyl site thereof.

13. The kit of claim 12, wherein said nucleic acid encodes AAV rep protein.

14. The kit of claim 12, wherein said termination codon is an amber codon, an opal codon or an ochre codon.

15. The kit of claim 12, wherein said cell is a 293 cell.

16. The kit of claim 12, wherein said nucleic acid encodes an AAV cap protein.

17. The kit of claim 12, wherein said introduced termination codon replaces a serine codon.

18. A method of producing adeno-associated virus (AAV), wherein the expression of AAV REP or CAP is regulated, comprising:
   (a) providing a host cell;
   (b) introducing a termination codon into a nucleic acid encoding REP or CAP and transforming said host cell with said nucleic to effect down regulated expression of REP or CAP;
   (c) further transforming said host cell with a vector plasmid comprising a transgene flanked by AAV ITRs;
   (d) then following steps (b) and (c), when AAV production is desired, transiently transforming said cell with a recombinant adenoviral vector that provides helper functions for the replication of AAV, said adenoviral vector carrying a tRNA, wherein said tRNA comprises an anticodon for said introduced termination codon and an amino acid for incorporation into a polypeptide during translation to suppress said introduced termination codon; and
   (e) retrieving AAV produced by said host cell.

19. The method of claim 18, wherein said termination codon is an amber codon, an opal codon or an ochre codon.

20. The method of claim 18, wherein said termination codon is introduced in the first half of the nucleic acid encoding REP or CAP.

21. The method of claim 18, wherein said introduced termination codon replaces a serine codon.

22. A method of producing adeno-associated virus (AAV), wherein the expression of AAV REP or CAP is regulated, comprising:
   (a) providing a host cell;
   (b) introducing a termination codon into a nucleic acid encoding REP or CAP and transforming said host cell with said nucleic to effect down regulated expression of REP or CAP;
   (c) further transforming said host cell with a vector plasmid comprising a transgene flanked by AAV ITRs;
   (d) then following steps (b) and (c), when AAV production is desired, transiently transforming said cell with a recombinant viral vector that provides helper functions for the replication of AAV, said viral vector carrying a tRNA, wherein said tRNA comprises an anticodon for said introduced termination codon and an amino acid for incorporation into a polypeptide during translation to suppress said introduced termination codon; and
   (e) retrieving AAV produced by said host cell.

23. The method of claim 22, wherein said termination codon is an amber codon, an opal codon or an ochre codon.

24. The method of claim 22, wherein said termination codon is introduced in the first half of the nucleic acid encoding REP or CAP.

25. The method of claim 22, wherein said introduced termination codon replaces a serine codon.

* * * * *

UNITED STATES PATENT AND TRADEMARK OFFICE
CERTIFICATE OF CORRECTION

PATENT NO.    : 6,586,208 B2
DATED         : July 1, 2003
INVENTOR(S)   : Brian A. Donahue et al.

It is certified that error appears in the above-identified patent and that said Letters Patent is hereby corrected as shown below:

<u>Title page, Item [54] and Column 1, line 1,</u>
Title, "USE OF SUPPRESSOR TRNA'S TO REGULATE CYTOTOXICITY DURING THE PRODUCTION OF RECOMBINANT GENE PRODUCTS" should read
-- USE OF SUPPRESSOR tRNA'S TO REGULATE CYTOTOXICITY DURING THE PRODUCTION OF RECOMBINANT GENE PRODUCTS --.

<u>Column 6,</u>
Line 15, "pol II" should read -- pol III --.

<u>Column 9,</u>
Line 59, "Pour" should read -- Four --.

<u>Column 10,</u>
Line 50, "adenoassociated" should read -- adeno-associated --.
Line 53, "Gohn" should read -- John --.

Signed and Sealed this

Fourteenth Day of October, 2003

JAMES E. ROGAN
*Director of the United States Patent and Trademark Office*

SEQUENCE LISTING

<160> NUMBER OF SEQ ID NOS: 9

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 1
gattaggtcc cctaggacct tgacgggcat c                                    31

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 2
ccacgagcac gtgcatgtgg                                                 20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 3
agattcgcga aaaactgat                                                  19

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 4
tcctggatcc actgcttctc ctaggtaatc cccttgtcca cga                       43

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 5
ccatttggca tgacactacg accaacacga tagcggttgt ctcggcgcac tcc            53

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 6

```
gctccggtcg actcacatgg ggtagagtca taatc                              35

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 7
cccggatcca aatatgacta cgtccggcgt tccatttggc atgacactac              50

<210> SEQ ID NO 8
<211> LENGTH: 116
<212> TYPE: DNA
<213> ORGANISM: Homo sapiens
<220> FEATURE:
<223> OTHER INFORMATION: serine tRNA gene

<400> SEQUENCE: 8
aagcttctta aggtagtcgt ggccgagtgg ttaaggcgat ggactctaaa tccattgggg   60 tctcccgcg caggttcgaa tcctgccgac tacgccatgg tttttgctcc ggatcc       116

<210> SEQ ID NO 9
<211> LENGTH: 118
<212> TYPE: DNA
<213> ORGANISM: Artificial Sequence
<220> FEATURE:
<223> OTHER INFORMATION: Description of Artificial Sequence: polylinker
      sequence

<400> SEQUENCE: 9
ttcgcgactt aattaacggt accgggcccc ccctcgaggt cgacggtatc gataagcttg   60
atatcgaatt cctgcagccc gggggatcca ctagttctag agcggccgcc acagctga   118
```